(12) United States Patent
Bhakuni et al.

(10) Patent No.: US 6,677,463 B1
(45) Date of Patent: Jan. 13, 2004

(54) SINGLE POT CONVERSION OF ARTEMISININ TO ARTESUNIC ACID

(75) Inventors: Rajendra Singh Bhakuni, Lucknow (IN); Atul Prakash Kahol, Lucknow (IN); Tarun Singh, Lucknow (IN); Suman Preet Singh Khanuja, Lucknow (IN)

(73) Assignee: Council of Scientific and Industrial Research, Delhi (IN)

( * ) Notice: Subject to any disclaimer, the term of this patent is extended or adjusted under 35 U.S.C. 154(b) by 0 days.

(21) Appl. No.: 10/315,921

(22) Filed: Dec. 10, 2002

(51) Int. Cl.$^7$ .................. C07D 323/00; C07D 325/00; C07D 493/18

(52) U.S. Cl. ........................................ 549/348; 549/349

(58) Field of Search .................................. 549/348, 349

(56) References Cited

U.S. PATENT DOCUMENTS 6,307,068 B1 * 10/2001 Li et al. ..................... 549/348

* cited by examiner

*Primary Examiner*—Taofiq Solola
(74) *Attorney, Agent, or Firm*—Natida P.B.A. Kumar, Esq.; Maryellen Feehery, Esq.; Reed Smith LLP

(57) ABSTRACT

The present invention provides a single pot process for the preparation of artesunic acid from artemisinin involving reduction followed by esterification of the reduced product at room temperature.

22 Claims, No Drawings

SINGLE POT CONVERSION OF ARTEMISININ TO ARTESUNIC ACID

FIELD OF INVENTION

The present invention relates to a single pot process for preparing artesunic acid from artemisinin. Artesunic acid is the 10 α-hemisuccinate ester of dihydroartemisinin. Artesunic acid and artesunate are customary names for dihydroartemisinin hemisuccinate and its sodium salt, respectively.

BACKGROUND OF THE INVENTION

Malaria is caused by protozoan parasites, notably *Plasmodium falciparum*. The range of drugs available in the market for prevention and treatment of malaria is limited, and there are problems of drug resistance. Artemisinin and its derivatives: artemether and arteether (oil soluble), artelinate and artesunate (water soluble), are a class of anti-malarial compounds derived from *Artemisia annua* which are now proving their promising activity and are being used for the treatment of uncomplicated/severe complicated/cerebral and multi drug resistant malaria. The chemistry and the anti-protozoal action of these compounds, described in the publications are listed as references cited.

The water-insoluble artesunic acid is customarily administered orally in the form of tablets or rectally in the for mn of suppositories, while the water-soluble artesunate is administered intravenously.

Artesunic acid together with a number of other $C_{10}$-ester and $C_{10}$-ether derivatives of dihydroartemisinin, were prepared for the first time by Chinese scientists at the end of 1979 to the beginning of 1980. Shaofeng et al., H Labeling of QHS Derivatives, Bull. Chin. Materia Medica 6 (4), 25–27 (1981) and Li et al., Synthesis of Ethers. Carboxylic esters and carbonates of Dihydroartemisinin, Acta Pharm. Sin 16(6), 429–39, 1981) describe the preparation of artesunic acid by acylation of dihydroartemisinin with succinic anhydride in pyridine. The above mentioned publications describe a general method for preparing various dihydroartemisinin $C_{10}$-esters and also provide a process for preparing artesunic acid in a yield of 60% by means of warming dihydroartemisinin and succinic anhydride in pyridine at 30° C. for 24 hours.

Ying et al. in the Synthesis of some carboxylic esters and carbonates of Dihydroartemisinin by using 4-(N,N-Dimethylamino)pyridine as an active acylation catalyst, Acta Chim Sinica 40 (6), 557–561 982) proposed an improved version of the acylation of dihydroartemisinin. The said publication described in detail with the aid of the preparation of dihydroartemisinin—10-valerate the aforesaid process. In this process dihydroartimisinin was dissolved in 1,2-dichloroethane and treated with valeric anhydride, 4-(N,N-dimethylamino)pyridine and triethylamine, and the mixture was stirred at room temperature until dihydroartemisinin had been used up. The reaction mixture was then acidified with dilute hydrochloric acid and the aqueous phase was separated off. The oily residue, obtained after washing and drying the organic phase was distilling off the solvent, was purified by chromatography on silica gel using petroleum ether 60–80° C. degree/ethyl acetate (10:1) as an eluent. The use of this procedure for the preparation of the artesunic acid from dihydroartemisinin with succinic anhydride and 4-(N,N-dimethylamino) pyridine afforded artesunic acid in a yield of 65% in 5 hours. U.S. Pat. No. 5,654,446 granted to Ognyanov et al. titled "Process for preparation of Dihydroartemisinin Hemisuccinate (artesunic acid)", dated Aug. 5, 1997 teaches a process for preparing $C_{10}$ α-artesunic acid by acylation of dihydroartemisinin with succinic anhydride, in the presence of trialkylamines and their mixture in a low boiling, neutral water miscible, inert organic solvent or solvent mixture at 20–60° C. in 0.5 hours and the artesunic acid is then isolated directly at pH 5 to 8 in 91.8 to 97.2% yield.

The above mentioned methods carry some disadvantages being less cost effective and more time consuming as compared to the present invention it should be noted that all the above referenced methods require two separate steps to convert artemisinin into 10-esters of dihydroartemisinin i.e. (a) reduction of artemisinin into dihydroartemisinin in the first pot following by isolation of dihydroartemisinin, and (b) esterification of dihydroartemisinin into different esters in the second pot.

Further, solvent pyridine or 1,2 dichloroethane and catalyst, 4(N,N-dimethylamino)pyridine used in these processes are not acceptable according to the health standard. Hence there is a need to provide a single step process that overcomes the above-mentioned disadvantages.

The present is able to overcome the shortcoming of the cited prior art processes being one pot conversion using artemisinin directly (rather than dihydroartemisinin as in above citations), using the process described at room temperature.

OBJECTS OF THE INVENTION

The main object of the present invention is to provide a single pot process for conversion of artemisinin to artesunic acid.

Another object of the present invention is to provide a process wherein reduction and esterification of artemisinin to obtain artesunic acid is carried out in a single pot.

Yet another object of the present invention is to provide a process wherein conversion of artemisinin to artesunic acid is carried out at room temperature.

SUMMARY OF THE INVENTION

Accordingly, the present invention provides a single pot process for the preparation of artesunic acid from artemisinin involving reduction followed by esterification of the reduced product at room temperature.

DETAILED DESCRIPTION OF THE INVENTION

The present invention provides a single pot process for preparing artesunic acid from artemisinin the said process comprising the steps of:

(a) dissolving artemisinin in a solvent at a temperature ranging between 20 to 35° C. to obtain a solution, adding a catalyst to the solution;

(b) adding a reducing agent to step (a) solution, stirring the mixture at a temperature ranging between 20 to 35° C. for about 0.5 h to 4 h to obtain the reduced product dihydroartemisinin;

(c) adding succinic anhydride and a base to the mixture of step (b) at a temperature ranging between 20 to 35° C.;

(d) stirring the mixture of step (c) at a temperature ranging between 20 to 35° C. for a time period of 1 h to 3 h;

(e) adding cold water to the mixture of step (d), adjusting the pH of the solution between 5 to 7, extracting the solution of pH 5 to 7 with a mixture of ethyl acetate and n-hexane, separating the organic layer;

(f) washing the organic layer of step (e) with water, drying the washed organic layer over anhydrous sodium sulphate, filtering, evaporating the organic layer to obtain a residue, and (g) purifying the residue of step (f) over silica gel column chromatography to obtain pure artesunic acid.

In an embodiment of the present invention, the two reactions, namely reduction of artemisinin to dihydroartemisinin and esterification of dihydroartemisinin are carried out in a single pot thereby avoiding the process of isolation of the intermediate dihydroartemisinin.

In another embodiment of the present invention, the solvent used in step (a) is selected from the group consisting of 1,4-dioxan or tetrahydrofuran.

In yet another embodiment of the present invention, the catalyst used in step (a) is selected from the group consisting of polyhydroxy compound or a cation exchange resin.

In still another embodiment of the present invention, the polyhydroxy compound used is dextrose.

In a further embodiment of the present invention, the w/w ratio of artemisinin and the catalyst is in the range of 1:2 to 1:5.

In one more embodiment of the present invention, the reducing agent used in step (b) is selected from the group consisting of sodium borohydride, lithium aluminium hydride, lithium tritertbutoxy aluminium gydride, lithium trimethoxy aluminium hydride, sodium trimethoxy borohydride, sodium bis-2-methoxy, ethoxy aluminium hydride or a mixture of lithium or sodium in alcohol or liquid ammonia.

In one another embodiment of the present invention, the reducing agent used is sodium borohydride.

In an embodiment of the present invention, the w/w ratio of artemisinin and sodium borohydride is in the range of 1:0.5 to 1:5.0.

In another embodiment of the present invention, the succinic anhydride used in step (c) is an esterifying agent.

In yet another embodiment of the present invention, the w/w ratio of artemisinin and succinic anhydride is in the range of 1:0.3 to 1:0.7.

In still another embodiment of the present invention, the w/w ratio of artemisinin and succinic anhydride is 1:0.5.

In a further embodiment of the present invention, the base used in step (c) is selected from the group consisting of triethylamine, sodium bicarbonate or anion exchange resin.

In one more embodiment of the present invention, the w/w ratio of artemisinin and the base is in the range of 1:1.2 to 1:7.

In one another embodiment of the present invention, the pH of the solution in step (e) is adjusted by adding acetic acid.

In an embodiment of the present invention, the extraction of crude artesunic acid from the solution in step (e) is carried out with a mixture of 40% ethyl acetate and n-hexane to avoid extraction of unwanted polar impurities.

In another embodiment of the present invention, the extraction using the mixture of 40% ethyl acetate and n-hexane may be performed more than once for complete extraction of artesunic acid.

In yet another embodiment of the present invention, the purification of crude artesunic acid in step (g) is carried out over silica gel column.

In still another embodiment of the present invention, the w/w ratio of crude artesunic acid and silica gel used is in the range of 1:4 to 1:5.

In a further embodiment of the present invention, the silica gel column is eluted using a gradient solvent mixture of 20–30% ethyl acetate in n-hexane.

In one more embodiment of the present invention, 96% w/w artesunic acid is obtained.

In one another embodiment of the present invention, the time required for conversion of artemisinin into artesunic acid is about 6 h to 10 h.

In a further embodiment of the invention, other 10 esters of dihydroartemisinin e.g. 10-propionate, chloroacetate and acetate were also prepared this improved one pot process.

In the process of the present invention, artemisinin and the catalyst, polyhydroxy compound or cation exchange resin were stirred in 1,4-dioxan or tetrahydrofuran for 5 minutes. Sodium borohydride was added slowly at room temperature (20–35° C.) and the reaction mixture was stirred for about 0.5–2 hours at room temperature. After completion of the reduction of artemisinin, without workup or the isolation of the dihydroartemisinin, succinic anhydride was added in the presence of a base at room temperature (20–35° C.). The reaction mixture was stirred further for about 1–3 hours at room temperature (20–35° C.). After completion of the esterification reaction, cold water was added. The Applicants experimentally found that if the pH of the solution is maintained between 6–7, it is conducive for extraction with ethyl acetate n-hexane mixture. Hence, the pH of the solution is adjusted between 6 to 7 by adding acetic acid. The solution having pH of 6–7 was then extracted with mixture of ethyl acetate n-hexane (3–4 times). The combined extract was washed with water. The ethyl acetate-hexane extract was dried over anhydrous sodium sulphate and removal of the solvent furnished impure artesunic acid. Silica gel column chromatography (1:4–5 ratio) of the impure artesunic acid using 20–30% ethyl acetate in n-hexane as an eluant furnished pure artesunic acid in 85–96% w/w yield.

The invention is further described with reference to the accompanying examples which are given by way of illustration and should not be construed to limit the scope of the present invention in any manner.

EXAMPLE 1

Artemisinin (500 mg) and polyhydroxy compound (dextrose, 2.5 g) are stirred in 1,4-dioxan (15 ml) at room temperature for 5 minutes. Sodium borohydride (2.5 g) is added slowly for 10 minutes and the reaction mixture is stirred for about 2 hours at room temperature (20–30° C.). After completion of the reaction (Checked by TLC), succinic anhydride (250 mg) and anion exchange (basic) resin (1.5 g) are added at room temperature and the reaction mixture is stirred further for 2 hours at room temperature. Cold water (50 ml) is added to the reaction mixture and pH is adjusted between 6–7 with dilute acetic acid and extracted with 40% ethyl acetate in hexane (3×25 ml). The combined extract is washed with water (50 ml). The ethyl acetate n-hexane extract is dried over anhydrous sodium sulphate and evaporation of the solvent yield 655 mg of crude artesunic acid which upon purification over silica gel (1:5 ratio) with 20–30% ethyl acetate in hexane, furnish pure artesunic acid in 93% w/w (465 mg) yield (according to CO-TLC). After drying the pure α-artesunic acid, mp 140–142° C. is charetrised by spectral analysis.

EXAMPLE 2

Artemisinin (500 mg), polyhydroxy compound (dextrose, 2.0 g) are stirred in 1,4-dixan (10 ml). Sodium borohydride (2.5 g) is added slowly for 10 minutes and the reaction mixture is stirred for about 2 hours at room temperature (20–30° C.). After completion of the reduction step, succinic anhydride (250 mg) and triethylamine (1 ml) are added and the reaction mixture is further stirred for 2 hours at room temperature (20–30 degree C.). After usual work up and purification of crude product (690 mg) through column chromatography (1:4 ratio) 91.2% pure artesunic acid is obtained.

EXAMPLE 3

Artemisinin (500 mg), polyhydroxy compound (dextrose, 2.0 g) are stirred in tetrahydrofuran (10 ml). Sodium borohydride (2.5 g) is added slowly for 10 minutes and the reaction mixture is stirred for about 2 hours at room temperature. After completion of the reduction step succinic anhydride (250 mg) and triethylamine (1 ml) are added and the reaction mixture is further stirred for 2 hours at room temperature. After usual work up and purification of the crude product (615 mg) through column chromatography 87.4% pure artesunic acid is obtained.

EXAMPLE 4

Artemisinin (500 mg) and polyhydroxy compound (dextrose, 2 g) are stirred in dioxan (15 ml) for 5 minutes. Sodium borohydride (2.4 gm) is added slowly and the reaction mixture is stirred for 2 hours at room temperature (20–30 degree C.). After completion of the reduction step succinic anhydride (250 mg) and sodium bicarbonate (3.5 g) are added and the reaction mixture is further stirred for 2 hours. After usual workup and purification of impure reaction product (650 mg), 89.6% w/w pure artesunic acid is obtained.

EXAMPLE 5

Artemisinin (500 mg) and cation exchange resin (1 g) are stirred in tetrahydrofuran (10 ml) at room temperature for 5 minutes. Sodium borohydride (250 mg) is added slowly for 10 minutes and the reaction mixture is stirred for about 30 minutes at room temperature (20–35 degree C.). After completion of the reaction succinic anhydride (250 mg) and triethylamine (0.7 ml) are added at room temperature and the reaction mixture is stirred further for 1 hours at room temperature. The resin is filtered. After usual workup and column chromatography of the crude product (710 mg), 480 mg of pure artesunic acid (yield=96% w/w) is obtained.

EXAMPLE 6

Artemisinin (500 mg) and cation exchange resin (1 g) are stirred in 1,4 dioxan (10 ml) at room temperature for 5 minutes. Sodium borohydride (250 mg) is added slowly for 10 minutes and the reaction mixture is stirred for about 30 minutes at room temperature (20–35 degree C.). After completion of the reaction succinic anhydride (250 mg) and triethylamine (0.7 ml) are added slowly at room temperature and the reaction mixture is stirred further for 1.25 hours at room temperature. After usual work up and purification of the crude artesunic acid (680 mg) pure product in 91.7% w/w is obtained.

EXAMPLE 7

Artemisinin (500 mg), cation exchange resin (10 g) are stirred in 1,4 dioxan (10 ml). Sodium borohydride (250 mg) is added slowly for 10 minutes and the reaction mixture is stirred for about 45 minutes at room temperature (20–35 degree C.). After completion of the reduction step succinic anhydride (250 mg) and sodium bicarbonate (2.5 g) are added and the reaction mixture is further stirred for 1.5 hours at room temperature (20–35 degree C.). After usual work up and purification of the crude artesunic acid (630 mg) pure product in 85% w/w yield is obtained.

EXAMPLE 8

Artemisinin (500 mg) and cation exchange resin (1 g) are stirred in tetrahydrofuran (15 ml) for 5 minutes. Sodium borohydride (2.4 gm) is added slowly and the reaction mixture is stirred for 45 minutes at room temperature (20–35 degree C.). After completion of the reduction reaction, succinic anhydride (245 mg) and sodium bicarbonate (3.5 g) are added and the reaction mixture is further stirred for 1.25 hours. After usual workup and purification of impure reaction product (650 mg), pure artesunic acid in 93% w/w yield is obtained.

EXAMPLE 9

Artemisinin (100 mg) and cation exchange resin (200 mg) are stirred in tetrahydrofuran (3ml) at room temperature for 5 minutes. Sodium borohydride (50 mg) is added slowly for 10 minutes and the reaction mixture is stirred for about 30 minutes at room temperature (20–35 degree C.). After completion of the reaction propionic anhydride (0.5 ml) and triethylamine (0.2 ml) are added at room temperature and the reaction mixture is stirred further for 1.5 hours at room temperature. After usual workup and purification of the crude products through preparative TLC 44 mg of pure dihydroartemisinin 10-propionate characterised by its spectral analysis is obtained.

EXAMPLE 10

Artemisinin (100 mg) and cation exchange resin (200 mg) are stirred in tetrahydrofuran (3 ml) at room temperature for 5 minutes. Sodium borohydride (50 mg) is added slowly for 10 minutes and the reaction mixture is stirred for about 30 minutes at room temperature (20–35 degree C.). After completion of the reaction chloroacetic anhydride (50 mg) and triethylamine (0.2 ml) are added at room temperature and the reaction mixture is stirred further for 1.5 hours at room temperature. After usual workup and purification of the crude products through preparative TLC 35 mg of pure dihydroartemisinin 10-chloroacetate characterized by its spectral analysis is obtained.

EXAMPLE 11

Artemisinin (100 mg) and cation exchange resin (200 mg) are stirred in tetrahydrofuran (3 ml) at room temperature for 5 minutes. Sodium borohydride (50 mg) is added slowly for 10 minutes and the reaction mixture is stirred for about 30 minutes at room temperature (20–35 degree C.). After completion of the reaction acetic anhydride (50 mg) and triethylamine (0.2 ml) are added at room temperature and the reaction mixture is stirred further for 1.5 hours at room temperature. After usual workup and purification of the crude products through preparative TLC 42 mg of pure dihydroartemisinin 10-acetate identified by its spectral analysis is obtained.

EXAMPLE 12

Artemisinin (5 g) and cation exchange resin (10 g) are stirred in tetrahydrofuran (60 ml) at room temperature for 5 minutes. Sodium borohydride (2.5 g) is added slowly for 20 minutes and the reaction mixture is stirred for about 1 hour at room temperature (20–35 degree C.). After completion of the reaction succinic anhydride (2.5 g) and triethylamine (6 ml) are added at room temperature and the reaction mixture is stirred further for 1.5 hours at room temperature. After usual workup and purification of the crude product (6.92 g) through CC pure artesunic acid in 94.6% w/w yield is obtained.

ADVANTAGES OF THE PRESENT INVENTION

1. The two pot reactions: reduction of artemisinin into dihydroartemismin and esterification of dihydroartemisinin to artesunic acid carried out in one pot avoids the process of isolation of dihydroartemisinin is avoided which saves chemicals, labour and losses of dihydroartemisinin in isolating it.
2. Conversion of artemisinin into artesunic acid in one pot takes place in about 2–5 hours and is a less time consuming method as compared to previously reported methods in which conversion of artemisinin into dihydroartemisinin in first pot followed by isolation of dihydroartemisinin and its esterification into artesunic acid in the second pot is also a long process.
3. The conversion of artemisinin into artesunic acid in one pot is carried out at room temperature (20–35 degree C.) and thereby avoids use of cooling unit.
4. The solvent used to carry out the reduction reaction is also being used in esterification and thus enabling the process cost effective.
5. The catalysts, polyhydroxy compound or cation exchange resin used to carry out the reduction of artemisinin into dihydroartemisinin at room temperature (20–35° C.) are cost effective.
6. The conversion of artemisinin into crude artesunic acid followed by workup and purification to yield pure product takes 6–10 hours as compared to previously reported methods (about 20–40 hours) and thus the process is less time consuming.
7. The yield of final product in the present invention i.e. pure artesunic acid is upto 96%, w/w.
8. Thus, this improved process which avoids the disadvantages of previously known process is suitable for the preparation of artesunic acid in large scale.

All publications and patent applications mentioned in the specification are indicative of the level of those skilled in the art to which this invention pertains. The contents of all publications, patents and patent applications are herein incorporated by reference to the same extent as if each individual publication, patent or patent application was specifically and individually indicated to be incorporated by reference.

What is claimed is:

1. A single pot process for preparing artesunic acid from artemisinin the said process comprising the steps of:
   (a) dissolving artemisinin in a solvent at a temperature ranging between 20 to 35° C. to obtain a solution, adding a catalyst to the solution,
   (b) adding a reducing agent to step (a) solution, stirring the mixture at a temperature ranging between 20 to 35° C. for about 0.5 h to 4 h to obtain the reduced product dihydroartemisinin,
   (c) adding succinic anhydride and a base to the mixture of step (b) at a temperature ranging between 20 to 35° C.,
   (d) stirring the mixture of step (c) at a temperature ranging between 20 to 35° C. for a time period of 1 h to 3 h,
   (e) adding cold water to the mixture of step (d), adjusting the pH of the solution between 5 to 7, extracting the solution of pH 5 to 7 with a mixture of ethyl acetate and n-hexane, separating the organic layer,
   (f) washing the organic layer of step (e) with water, drying the washed organic layer over anhydrous sodium sulphate, filtering, evaporating the organic layer to obtain a residue, and
   (g) purifying the residue of step (f) over silica gel column chromatography to obtain pure artesunic acid.

2. A process as claimed in claim 1, wherein the two reactions, namely reduction of artemisinin to dihydroartemisinin and esterification of dihydroartemisinin are carried out in a single pot thereby avoiding the process of isolation of the intermediate dihydroartemisinin.

3. A process as claimed in claim 1, wherein in step (a) the solvent used is selected from the group consisting of 1,4-dioxan and tetrahydrofuran.

4. A process as claimed in claim 1, wherein in step (a) the catalyst used is selected from the group consisting of a polyhydroxy compound and a cation exchange resin.

5. A process as claimed in claim 4, wherein the polyhydroxy compound used is dextrose.

6. A process as claimed in claim 1, wherein the w/w ratio of artemisinin and the catalyst is in the range of 1:2 to 1:5.

7. A process as claimed in claim 1, wherein in step (b) the reducing agent is selected from the group consisting of sodium borohydride, lithium aluminium hydride, lithium tritertbutoxy aluminium gydride, lithium trimethoxy aluminium hydride, sodium trimethoxy borohydride, sodium bis-2-methoxy, ethoxy aluminium hydride and a mixture of lithium or sodium in alcohol or liquid ammonia.

8. A process as claimed in claim 7, wherein the reducing agent used is sodium borohydride.

9. A process as claimed in claim 8, wherein the w/w ratio of artemisinin and sodium borohydride is in the range of 1:0.5 to 1:5.0.

10. A process as claimed in claim 1, wherein in step (c) succinic anhydride acts as an esterifying agent.

11. A process as claimed in claim 1, wherein the w/w ratio of artemisinin and succinic anhydride is in the range of 1:0.3 to 1:0.7.

12. A process as claimed in claim 11, wherein the w/w ratio of artemisinin and succinic anhydride is 1:0.5.

13. A process as claimed in claim 1, wherein in step (c) the base used is selected from the group consisting of triethylamine, sodium bicarbonate and anion exchange resin.

14. A process as claimed in claim 13, wherein the w/w ratio of artemisinin and the base is in the range of 1:1.2 to 1:7.

15. A process as claimed in claim 1, wherein in step (e) the pH of the solution is adjusted between 6 to 7 by adding acetic acid.

16. A process as claimed in claim 1, wherein in step (e) the extraction of crude artesunic acid from the solution is carried out with a mixture of 40% ethyl acetate and n-hexane to avoid extraction of unwanted polar impurities.

17. A process as claimed in claim 16, wherein the extraction using the mixture of 40% ethyl acetate and n-hexane is performed one or more times for complete extraction of artesunic acid.

18. A process as claimed in claim 1, wherein in step (g) the purification of crude artesunic acid is carried out over silica gel column.

19. A process as claimed in claim 18, wherein the w/w ratio of crude artesunic acid and silica gel used is in the range of 1:4 to 1:5.

20. A process as claimed in claim 18, wherein the silica gel column is eluted using a gradient solvent mixture of 20–30% ethyl acetate in n-hexane.

21. A process as claimed in claim 1, wherein 96% w/w artesunic acid is obtained.

22. A process as claimed in claim 1, wherein the time required for conversion of artemisinin into artesunic acid is about 6 h to 10 h.

* * * * *